United States Patent [19]

Deshmukh

[11] 4,040,784

[45] Aug. 9, 1977

[54] METHOD FOR CHECKING THE ACCURACY OF A TEST, USING A SERUM-SOLUBLE CHOLESTEROL COMPOUND

[76] Inventor: Arvind D. Deshmukh, 1011 Pearl St., Santa Monica, Calif. 90405

[21] Appl. No.: 716,615

[22] Filed: Aug. 23, 1976

[51] Int. Cl.² ............................................. G01N 33/16
[52] U.S. Cl. .................................................. 23/230 B
[58] Field of Search ....................................... 23/230 B

[56] References Cited

U.S. PATENT DOCUMENTS 3,859,047   1/1975   Klein .................................. 23/230 B

*Primary Examiner*—Robert M. Reese
*Attorney, Agent, or Firm*—Nilsson, Robbins, Dalgarn & Berliner

[57] ABSTRACT

Water and serum soluble cholesterol compounds are prepared by reactively combining a lower acid ester of cholesterol with a peptide or protein as solubilizing agent. The water-soluble cholesterol compounds can be lyophilized and added to serum as a standard for the determination of cholesterol in biological fluids by traditional saponification methods.

3 Claims, No Drawings

METHOD FOR CHECKING THE ACCURACY OF A TEST, USING A SERUM-SOLUBLE CHOLESTEROL COMPOUND

FIELDS OF THE INVENTION

The fields of art to which the invention pertains include the field of steroid chemistry and the field of biological testing.

BACKGROUND AND SUMMARY OF THE INVENTION

In recent years, it has become common in clinical laboratories to test for the level of cholesterol in blood serum samples. The measured levels of cholesterol in the blood are referred to as total serum cholesterol, and include all those cholesterol compounds which are present in the blood such as cholesterol and its derivatives dihydrocholesterol and 7-dihydrocholesterol, whether present in their free from or in the form of esters with the fatty acids normally present in the blood. There are a number of methods which can be utilized for the determination of total cholesterol in biological fluids. In accordance with the method of Abell et al, the serum is treated with alcoholic potassium hydroxide to liberate the cholesterol from its lipoprotein complexes and to saponify the natural cholesterol esters. The saponified cholesterol is extracted into a measured volume of petroleum ether and then an aliquot is subjected to color reaction utilizing a modified LibermannBurchard reagent. Reference can be made to the journal "STANDARDIZED METHODS OF CLINICAL CHEMISTRY", vol. 2, pages 26 etc. (1958) by L. L. Abell et al. The optical density of each sample is read against a blank in a photoelectric colorimeter. The level of cholesterol equivalent to the optical density is calculated by comparing the optical density to that of a standard containing a known amount of cholesterol.

For most serum clinical chemistry procedures, it is desirable to use one serum based reference control for a variety of tests. However, cholesterol, per se, is not soluble in biological fluids such as serum. To overcome such deficiency, the prior art has attempted to solubilize the cholesterol by forming organic salts thereof. See, for example, U.S. Pat. No. 3,859,047 to Klein. However, the level of solubility achieved is insufficient to provide sufficiently high concentrations for all desired uses. For example, even with the use of a surfactant such as Triton X-100 (polyethyleneglycol ether of monoisoocytyl phenol, by Rohm & Haas, Inc., Philadelphia, Pa.) a useful concentration of less than 0.1 gram per deciliter is provided. The sample becomes turbid at significantly higher concentrations, and since a colorimetric procedure is utilized, gross errors can be introduced.

The present invention provides serum-soluble cholesterol compounds and methods for their preparation, which can be lyophilized and added in high concentration to blood serum. A turbid-free clinical chemistry control is thus provided having a high cholesterol value and which can be assayed by the standard procedure. Concentration levels of up to 1 gram of cholesterol equivalent per deciliter are easily prepared. Furthermore, the cholesterol compounds of this invention do not interfere with other analytical test making them highly useful in a multiple serum control.

More specifically, the present cholesterol compound is defined by at least one acid ester of cholesterol reactively combined with a peptide or protein as solubilizing agent. Reaction is with the amino group derived from the peptide or protein (i.e., as a part thereof). The acid ester is an ester of a lower dicarboxylic acid having 2-7 carbon atoms in its longest chain (including the acid carbon atoms).

DETAILED DESCRIPTION

As an initial step in the preparation of a water soluble, serum-soluble cholesterol compound useful herein, there is first formed an acid ester of cholesterol having the formula:

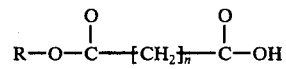

in which R is a cholesteryl radical and $n$ is 0–5. The above esters can be prepared by reacting cholesterol with the corresponding dibasic acid. Examples of the resultant alkyl monoacid esters include cholesteryl hydrogen succinate, cholesteryl hydrogen adipate, cholesteryl hydrogen oxalate, cholesteryl hydrogen malonate, cholesteryl hydrogen glutanate, cholesteryl hydrogen pimelate, and the like.

The acid ester of cholesterol can be reacted directly with the amine component of the amino residue of a protein or peptide in accordance with the following equation.

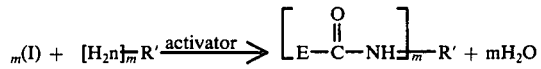

in which $m$ is 1 to 100, R' is from a peptide or protein having the amino residue $R'-NH_{2_M}$, and E is the cholesteryl ester function:

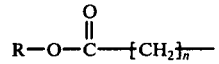

The amino group is from a peptide, preferably a high molecular weight peptide, or from a protein, and in this regard it is particularly preferred to use albumin, such as human, rabbit or bovine albumin, but preferably the latter. Bovine albumin has 59 lysine residues, permitting a large number of cholesterol radicals to be conjugated therewith. Broadly, materials such as polylysine, polyarginine, small peptides having 6 or more amino acids and which contain basic groups (e.g., lysine) as a constituent, can all be used. Reference can be made to "Biological Chemistry", by H. R. Mahler and E. H. Cordes, Harper Row Pub., N.Y., pages 9–120, for a description of suitable peptides, which description is incorporated herein by reference.

In conducting the foregoing reaction, an activating agent should be used and such can be defined as a material which facilitates reaction between an acid and an amine and which has minimum reaction with cholesterol. Such materials are well known in the field of protein and peptide synthesis and one can refer to "BASIC PRINCIPLES OF ORGANIC CHEMISTRY" by Roberts and Cassiero, (1964), pages 702–723, published by W. A. Benjamin, Inc., incorporated herein be reference. Specific examples include carbodiimides such as dicyclohexyl carbodiimide, 1-ethyl-3-(3'-dimethylaminopropyl) carbodiimide, Woodward Reagent K-(N-ethyl-5-phenylisoxazolium-3'-sulfate), alkylchloroformate such ethylchloroformate, n-butylchloroformate, isobutylchloroformate, and the like.

In the foregoing preparation, the peptide or protein can be dissolved in distilled water and a water-miscible organic solvent added thereto, such as dimethylsulfoxide, dimethyl formamide, tetrahydrofuran, acetone, dioxane, acetonitrile, or the like. The cholesterol ester component and activating agent can then be added to the well mixed solution. The resultant solution can be dialyzed against running water for several days followed by lyophilization to produce a powdery material. In general, it is desirable to conduct the reaction under alkaline conditions. Accordingly, a small amount of sodium hydroxide or the like can be added to the reaction solution.

The resultant lyophilized substances can form stable aqueous solutions which dissolve in biological fluids such as whole serum to form clear, stable solutions yielding accurate, positive results with both saponification and enzymatic test procedures. The consistency of results is unaffected by other substances normally present in biological fluids and the cholesterol compounds of the invention when added to biological fluids such as serum, do not interfere with other analytical tests usually carried out thereon thus making them highly useful as a cholesterol member of multiple component analytical standards and control materials. Advantageously, the cholesterol compounds of the invention are readily soluble in water in an amount equivalent to about 10 grams of cholesterol equivalent per 100 milliliter, and in biological fluids such as cholesterolfree serum in an amount equivalent to about 7 grams of free cholesterol per 100 milliliters. For common analytical procedures, an amount of cholesterol compound equivalent to form about 50 milligrams to about 400 milligrams of cholesterol per 100 milliliter, dissolved in 5 ml. water is used to reconstitute a lyophilized 5 ml. sample of the biological fluid to be tested. These amounts are chosen as they represent the practical levels of cholesterol in the blood. Aliquots are from 0.10 to 0.50 ml. of the reconstituted serum are utilized as standards for most analytical procedures. The cholesterol compounds of the present invention may be supplied per se in dry form or as standard stock solutions.

The following examples further illustrate the invention.

EXAMPLE 1

20.25 Grams (41.8 mmoles) of cholesteryl hydrogen succinate (sold by Aldrich Chemicals) and 19.8 ml (83.4 mmoles) of tributylamine were dissolved in 540 ml of Dioxane. The solution was cooled and treated with 5.3 ml (5.7 g, 41.7 mmoles) of isobutyl chloroformate. The reaction was permitted to proceed in the cold for 30 minutes, and then the mixture was added in one portion to a stirred, cooled solution of 50.0 g (41.7 moles) of bovine serum albumin in 1100 ml of water, 750 ml of p-dioxane, and 50 ml of 1 N NaOH. Stirring and cooling was continued for 6 hours. The material was then dialyzed against water and lyophilized to yield a stable white powder useful as a cholesterol standard.

EXAMPLES 2-6

The procedure of Example 1 can be repeated by substituting respectively molar equivalent amounts of the corresponding cholesterol derivative of the dibasic acids, oxalic, malonic, glutamic or phthalic for the succinate.

EXAMPLE 7

In a non-enzymatic method of test, 1.5 Grams of the cholesterol succinic derivative can be added to an assayed control serum with a cholesterol value of 85 mgs %. Values before and after addition of the cholesterol reagent determined by the Zak (Standard Methods in Clinical Chemistry, ed. Meites, S. Academic Press, N.Y. 1965, vol. 5, p. 79) procedure are as follows:

| Before Addition | After Addition | % Recovery |
| --- | --- | --- |
| 85 mg% | 438 mg% | 101.2% |

The cholesterol additive in the above cases give a %C.V. of 3.2, as used in the method described.

I claim:

1. In a method for checking the accuracy of a test for the quantitative determination of the cholesterol content of a biological fluid wherein said test is conducted on a standard comprising a solution in said biological fluid of a known quantity of a serum-soluble cholesterol compound, the improvement in accordance with which said cholesterol compound is at least one ester of cholesterol reactively combined with a peptide or protein solubilizing agent, said ester being an ester of a lower dicarboxylic acid having 2 to 5 carbon atoms in its longest chain.

2. The improvement of claim 1 wherein said cholesterol compound has the formula

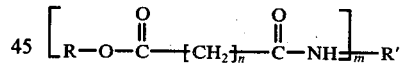

in which R is a cholesteryl radical, $n$ is 0-3, $m$ is 1-100 and

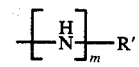

is a peptide or protein having the amino residue

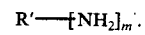

3. The improvement of claim 2 wherein $n$ is 2.

* * * * *

UNITED STATES PATENT AND TRADEMARK OFFICE
CERTIFICATE OF CORRECTION

PATENT NO. : 4,040,784
DATED : August 9, 1977
INVENTOR(S) : Arvind D. Deshmukh

It is certified that error appears in the above-identified patent and that said Letters Patent are hereby corrected as shown below:

Col. 1, line 30, "LibermannBurchard" should be --Libermann Burchard--.

Col. 2, line 33, "$H_2n$" should be --$H_2N$--.

Col. 2, line 36, "$R'-NH_{2_M}$" should be --$R'-NH_{2_m}$--.

Col. 3, line 32, "cholesterolfree" should be --cholesterol-free--.

Signed and Sealed this

Twenty-second Day of May 1979

[SEAL]

Attest:

RUTH C. MASON
Attesting Officer

DONALD W. BANNER
Commissioner of Patents and Trademarks